(12) United States Patent
Yue

(10) Patent No.: US 6,706,718 B2
(45) Date of Patent: Mar. 16, 2004

(54) 3-(2,4-DIMETHYLTHIAZOL-5-YL)INDENO[1,2-C]PYRAZOL-4-ONE DERIVATIVES AND THEIR USES

(75) Inventor: Eddy W. Yue, Landenberg, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/000,820

(22) Filed: Nov. 30, 2001

(65) Prior Publication Data

US 2002/0107274 A1 Aug. 8, 2002

Related U.S. Application Data

(60) Provisional application No. 60/251,213, filed on Dec. 1, 2000.

(51) Int. Cl.[7] .................. A61K 31/427; A61K 31/5377; C07D 413/14; C07D 417/04
(52) U.S. Cl. .............................. 514/254.04; 514/236.8; 514/326; 514/365; 544/133; 544/367; 546/209; 548/181
(58) Field of Search .......................... 548/181; 514/365, 514/326, 236.8, 254.04; 546/209; 544/133, 367

(56) References Cited

U.S. PATENT DOCUMENTS

| | | | |
|---|---|---|---|
| 6,107,305 A | 8/2000 | Misra et al. | |
| 6,114,365 A | 9/2000 | Pevarello et al. | |
| 6,407,103 B2 * | 6/2002 | Nugiel et al. | 514/232.8 |
| 2001/0027195 A1 | 10/2001 | Nugiel et al. | |

FOREIGN PATENT DOCUMENTS

| | | |
|---|---|---|
| GB | 2223946 A | 4/1990 |
| WO | WO99/54308 | 10/1999 |
| WO | WO 02/46182 A1 | 6/2002 |

OTHER PUBLICATIONS

Mani et al., Exp. Opin. Invest. Drugs, 2000, 9 (8), 1849–1870.
Jiang et al., Proc. Natl. Acad. Sci. USA, 1993, 90, 9026–9030.
Quaraishi, IL Farmaco, 1989, 44, 753–757.
Hosoi et al., J. Biochem., 1995, 117, 741–749.
Kamb et al., Science, 1994, 264, 436–440.
Bible et al., Cancer Research, 1997, 57, 3375–3380.
Russo et al., Nature, 1996, 382, 325–331.
Sherr, Cell, 1993, 73, 1059–1065.
Wang et al., Nature, 1990, 343, 555–557.
Chem Abstracts: JP60–130521/PN, 1985.
Chem Abstracts: JP 62–099361/PN, 1987.

* cited by examiner

*Primary Examiner*—Laura L. Stockton
(74) *Attorney, Agent, or Firm*—Elliott Korsen

(57) ABSTRACT

The present invention relates to 3-(2,4-dimethylthiazol-5-yl)indeno[1,2-c]pyrazol-4-ones of formula I:

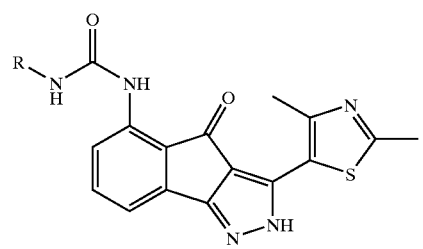

which are potent inhibitors of cyclin dependent kinases.

This invention also provides a novel method of treating cancer or other proliferative diseases by administering a therapeutically effective amount of one of these compounds or a pharmaceutically acceptable salt form thereof. Alternatively, one can treat cancer or other proliferative diseases by administering a therapeutically effective combination of one of the compounds of the present invention and one or more other known anti-cancer or anti-proliferative agents.

22 Claims, No Drawings

3-(2,4-DIMETHYLTHIAZOL-5-YL)INDENO[1, 2-C]PYRAZOL-4-ONE DERIVATIVES AND THEIR USES

This application claims priority from provisional U.S. Application Serial No. 60/251,213, filed Dec. 1, 2000, incorporated herein by reference in its entirety.

FIELD OF THE INVENTION

This invention relates generally to novel 3-(2,4-Dimethylthiazol-5-yl)indeno[1,2-c]pyrazol-4-one derivatives which are useful as cyclin dependent kinase (cdk) inhibitors, pharmaceutical compositions comprising the same, methods for using the same for treating proliferative diseases, and intermediates and processes for making the same.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a diverse set of cellular signals both within the cell and from external sources. A complex network of tumor promoting and suppressing gene products are key components of this cellular signaling process. Over expression of the tumor promoting components or the subsequent loss of the tumor suppressing products will lead to unregulated cellular proliferation and the generation of tumors (Pardee, Science 246:603–608, 1989).

Cyclin dependent kinases (cdks) play a key role in regulating the cell cycle machinery. These complexes consist of two components: a catalytic subunit (the kinase) and a regulatory subunit (the cyclin). To date, nine kinase subunits (cdk 1–9) have been identified along with several regulatory subunits (cyclins A–H).(A. M. Senderowicz and E. A. Sausville Journal of the National Cancer Institute (2000), 92 (5), 376–387; and S. Mani; C. Wang; K. Wu; R. Francis; R. Pestell Exp. Opin. Invest. Drugs (2000) 9(8), 1849–1870).

Each kinase associates with a specific regulatory partner and together make up the active catalytic moiety. Each transition of the cell cycle is regulated by a particular cdk complex: G1/S by cdk2/cyclin E, cdk4/cyclin D1 and cdk6/cyclinD2; S/G2 by cdk2/cyclin A and cdk1/cyclin A; G2/M by cdk1/B. The coordinated activity of these kinases guides the individual cells through the replication process and ensures the vitality of each subsequent generation (Sherr, Cell 73:1059–1065, 1993; Draetta, Trends Biochem. Sci. 15:378–382, 1990).

An increasing body of evidence has shown a link between tumor development and cdk related malfunctions. Over expression of the cyclin regulatory proteins and subsequent kinase hyperactivity have been linked to several types of cancers (Jiang, Proc. Natl. Acad. Sci. USA 90:9026–9030, 1993; Wang, Nature 343:555–557, 1990). More recently, endogenous, highly specific protein inhibitors of cdks were found to have a major affect on cellular proliferation (Kamb et al, Science 264:436–440, 1994; Beach, Nature 336:701–704, 1993). These inhibitors include p16$^{INK4}$ (an inhibitor of cdk4/D1), p21$^{CIP1}$ (a general cdk inhibitor), and p27$^{KIP1}$ (a specific cdk2/E inhibitor). A recent crystal structure of p27 bound to cdk2/A revealed how these proteins effectively inhibit the kinase activity through multiple interactions with the cdk complex (Pavletich, Nature 382:325–331, 1996). These proteins help to regulate the cell cycle through specific interactions with their corresponding cdk complexes. Cells deficient in these inhibitors are prone to unregulated growth and tumor formation.

Protein kinases, in particular, CDK, play a role in the regulation of cellular proliferation. Therefore, CDK inhibitors could be useful in the treatment of cell proliferative disorders such as cancer, familial adenomatosis polyposis, neuro-fibromatosis, psoriasis, fungal infections, endotoxic shock, trasplantaion rejection, vascular smooth cell proliferation associated with atherosclerosis, pulmonary fibrosis, arthritis glomerulonephritis and post-surgical stenosis and restenosis (U.S. Pat. No. 6,114,365). CDKs are also known to play a role in apoptosis.

Therefore CDK inhibitors, could be useful in the treatment of useful of cancer; viral infections, for example, herpevirus, poxvirus, Epstein-Barr virus, Sindbis virus and adenovirus; prevention of AIDS development in HIV-infected individuals; autoimmune diseases, for example, systemic lupus, erythematosus, autoimmune mediated glomerulonephritis, rheumatoid arthritis, psoriasis, inflammatory bowel disease, and autoimmune diabetes mellitus; neurodegenerative disorders, for example, Alzheimer's disease, AIDS-related dementia, Parkinson's disease, amyotrophic lateral sclerosis, retinitis pigmentosa, spinal muscular atrophy and cerebellar degeneration; myelodysplastic syndromes, aplastic anemia, ischemic injury associated with myocardial infarctions, stroke and reperfusion injury, arrhythmia, atherosclerosis, toxin-induced or alcohol related liver diseases, hematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain (U.S. Pat. No. 6,107,305).

It has also been discovered that some cyclin-dependent kinase inhibitors can be used in combination therapy with some other anticancer agents. For example, the cytotoxic activity of the cyclin-dependent kinase inhibitor, flavopiridol, has been used with other anticancer agents in cancer combination therapy. Cancer Research, 57, 3375 (1997).

Also, it has recenly been disclosed that CDK inhibitors may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse (U.S. Pat. No. 6,107,305).

Furthermore, it has recently been discovered that cdk5 is involved in the phosphorylation of tau protein, and therefore CDK inhibitors may be useful in the treatment of Alzheimer's disease (J. Biochem., 117, 741–749, 1995).

This body of evidence has led to an intense search for small molecule inhibitors of the cdk family as an approach to cancer chemotherapy. There are no known examples of molecules related to the current invention which describe 5-substituted-indeno[1,2-c]pyrazoles as cdk inhibitors. There is one case describing indeno[1,2-c]pyrazoles having anticancer activity. There are two other examples which describe indeno[1,2-c]pyrazoles having unrelated utilities and structures.

A series of indeno[1,2-c]pyrazoles having anticancer activity are described in JP 60130521 and JP 62099361 with the following generic structure:

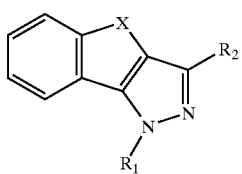

No substitution is claimed on the indenophenyl portion of the molecule and the molecules are not indicated to be cdk inhibitors. In addition, we discovered that substitution at the 5-position was critical for cdk inhibitory activity.

A series of indeno[1,2-c]pyrazoles having herbicidal activity are described in GB 2223946 with the following generic structure:

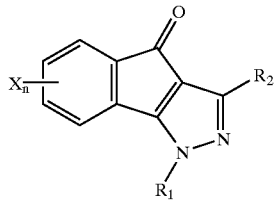

The above compounds differ from the presently claimed invention in $X_n$ is defined as halo, alkyl, haloalkyl, and haloalkoxy; n=0–2. In addition, $R_1$ is defined as acyl and $R_2$ is defined as alkyl or cycloalkyl.

A series of 1-(6'-substituted-4'-methylquinol-2'-yl)-3-methylindeno[1,2-c]pyrazoles having CNS activity are described by Quraishi, Farmaco 44:753-8, 1989 with the following generic structure:

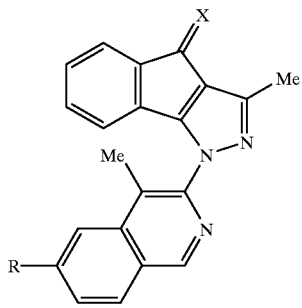

Compounds of this series are not considered to be part of the presently claimed invention.

Furthermore, Nugiel et al, International Application Number WO 99/54308, published Oct. 28, 1999, discloses a class of indeno[1,2-c]pyrazol-4-ones as cyclin dependent kinase (CDK) inhibitors for the potential treatment of cancer. Although, WO 99/54308 generally discloses indeno[1,2-c] pyrazol-4-one compounds, the compounds of this invention, or the unexpected activity of the compounds of this invention, are not specifically disclosed.

SUMMARY OF THE INVENTION

The present invention describes a class of 3-(2,4-Dimethylthiazol-5-yl)indeno[1,2-c]pyrazol-4-ones or pharmaceutically acceptable salt forms thereof that are potent inhibitors of the class of enzymes known as cyclin dependent kinases, which relate to the catalytic subunits cdk 1–9 and their regulatory subunits know as cyclins A—H.

This invention is a class of 3-(2,4-Dimethylthiazol-5-yl) indeno[1,2-c]pyrazol-4-ones which exhibit remarkable and unexpected improvements as cancer therapeutic agents compared to the compounds disclosed in WO 99/54308. The compounds of this invention are 3-(2,4-dimethylthiazol-5-yl)-5-(substituted carbamoylamino)indeno[1,2-c]pyrazol-4-ones which can be represented by formula I:

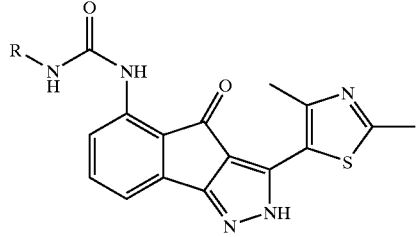

wherein R is defined below or pharmaceutically acceptable salts thereof are cyclin dependent kinase inhibitors.

DETAILED DESCRIPTION OF PREFERRED EMBODIMENTS

The compounds of this invention all exhibited outstanding enzyme inhibitory activity. The most preferred compounds of this invention show excellent activity against tumor cells growing in culture; however, normal cells as represented by the fibroblast AG1523 are comparatively spared. The most preferred compounds of this invention have excellent inhibitory activity against CDK2/E which translates into good cellular activity in the HCT116 colon cancer cell line. In addition, these compounds show good selectivity for HCT116 tumor cells over normal fibroblast cells (AG1523).

[1] The present invention, in a first embodiment, describes novel compounds of formula (I):

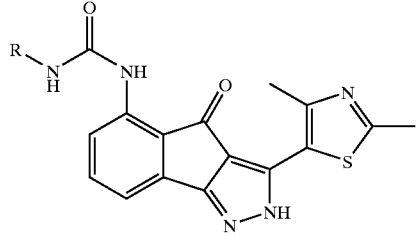

or stereoisomers thereof, N-Oxides thereof, pharmaceutically acceptable salts thereof, and prodrugs thereof, wherein:

R is independently at each occurrence selected from the group: H, $NR^1R^2$, $NR^1C(O)R^3$, $NR^1C(O)OR^5$, NHC(O)$NR^1R^2$, NHC(S)$NR^1R^2$, and 5–10 membered heterocycle containing from 1–4 heteroatoms selected from O, N, and S, wherein the heterocycle is substituted with 0–4 $R^4$ substituents;

$R^1$ is selected from the group: H, $C_{1-4}$ haloalkyl, $C_{1-4}$ alkyl, phenyl, and benzyl;

$R^2$ is selected from the group: H, $C_{1-4}$ alkyl, phenyl, and benzyl;

alternatively, $R^1$ and $R^2$, together with the nitrogen atom to which they are attached, form a 4–8 membered heterocycl group or a 4–8 membered heterocyclenyl group containing an additional 0–1 N, S, or O atom, wherein the heterocycl or heterocyclenyl group is substituted with 0–4 $R^4$ substituents;

$R^3$ is selected from the group: H, halo, —CN, $C_{1-4}$ haloalkyl, $C_{1-4}$ alkyl, phenyl, and benzyl; and $R^4$ is selected from the group: halo, —CN, $C_{1-4}$ haloalkyl, $C_{1-4}$ alkyl, phenyl, and benzyl.

$R^5$ is selected from the group: H, $C_{1-4}$ alkyl, phenyl, and benzyl.

[2] In a preferred embodiment, the present invention provides a novel compound of embodiment [1], wherein:

R is a 5–10 membered heterocycle containing from 1–4 heteroatoms selected from O, N, and S, wherein the heterocycle is substituted with 0–3 $R^4$ substituents.

[3] In a preferred embodiment, the present invention provides a novel compound of embodiment [1], wherein:

R is a 5–10 membered heterocycle containing from 1–4 heteroatoms selected from O, N, and S, wherein the heterocycle is substituted with 0–2 $R^4$ substituents.

[4] In a preferred embodiment, the present invention provides a novel compound of embodiment [1], wherein:

R is a 5–10 membered heterocycle containing from 1–4 heteroatoms selected from O, N, and S, wherein the heterocycle is substituted with a $R^4$ substituent.

[5] In a preferred embodiment, the present invention provides a novel compound of embodiment [1], wherein:

R is a 5–6 membered hetroaryl, heterocyclyl, or heterocyclenyl group, substituted with 0–3 $R^4$ substituents.

[6] In a preferred embodiment, the present invention provides a novel compound of embodiment [1], wherein:

R is H or $NR^1R^2$;

$R^1$ is selected from the group: H, $C_{1-4}$ alkyl, phenyl, and benzyl;

$R^2$ is selected from the group: H, $C_{1-4}$ alkyl, phenyl, and benzyl;

alternatively, $R^1$ and $R^2$, together with the nitrogen atom to which they are attached, form a 4–8 membered heterocycl group or a 4–8 membered heterocyclenyl group containing an additional 0–1 N, S, or O atom, wherein the heterocycl or heterocyclenyl group is substituted with 0–3 $R^4$ substituents; and $R^4$ is selected from the group:, halo, —CN, $C_{1-4}$ haloalkyl, $C_{1-4}$ alkyl, phenyl, and benzyl.

[7] In a preferred embodiment, the present invention provides a novel compound of embodiment [1], wherein:

R is H or $NR^1R^2$;

$R^1$ is selected from the group: H, $C_{1-4}$ alkyl, phenyl, and benzyl; and $R^2$ is selected from the group: H, $C_{1-4}$ alkyl, phenyl, and benzyl.

[8] In a preferred embodiment, the present invention provides a novel compound of embodiment [1], wherein:

R is H or $NR^1R^2$;

$R^1$ and $R^2$, together with the nitrogen atom to which they are attached, form a 4–8 membered heterocycl group containing an additional 0–1 N, S, or O atom, wherein the heterocycl is substituted with 0–3 $R^4$ substituents; and $R^4$ is selected from the group:, halo, —CN, $C_{1-4}$ haloalkyl, $C_{1-4}$ alkyl, phenyl, and benzyl.

[9] In a preferred embodiment, the present invention provides a novel compound of embodiment [1], wherein:

R is H or $NR^1R^2$;

$R^1$ and $R^2$, together with the nitrogen atom to which they are attached, form a 4–8 membered heterocyclyl group containing an additional 0–1 N, S, or O atom, wherein the heterocyclyl is substituted with 0–2 $R^4$ substituents; and $R^4$ is selected from the group:, halo, —CN, $C_{1-4}$ haloalkyl, $C_{1-4}$ alkyl, phenyl, and benzyl.

[10] In a preferred embodiment, the present invention provides a novel compound of embodiment [1], wherein:

$R^1$ and $R^2$, together with the nitrogen atom to which they are attached, form a heterocyclyl group selected from the group consiting of pyrrolidinyl, imidazolidinyl, pyrazolidinyl, piperidinyl, morpholinyl, thiomorpholinyl, and piperazinyl, wherein the heterocyclyl is substituted with 0–3 $R^4$ substituents; and $R^4$ is selected from the group:, halo, —CN, $C_{1-4}$ haloalkyl, $C_{1-4}$ alkyl, phenyl, and benzyl.

[11] In a preferred embodiment, the present invention provides a novel compound of embodiment [1], wherein:

$R^1$ and $R^2$, together with the nitrogen atom to which they are attached, form a heterocyclyl group selected from the group consiting of piperidinyl, morpholinyl, and piperazinyl, wherein the heterocyclyl is substituted with 0–3 $R^4$ substituents; and $R^4$ is selected from the group:, halo, —CN, $C_{1-4}$ haloalkyl, $C_{1-4}$ alkyl, phenyl, and benzyl.

[12] In a preferred embodiment, the present invention provides a novel compound of embodiment [1], wherein:

R is H or $NR^1R^2$;

$R^1$ and $R^2$, together with the nitrogen atom to which they are attached, form a 4–8 membered heterocyclenyl group containing an additional 0–1 N, S, or O atom, wherein the heterocyclenyl is substituted with 0–3 $R^4$ substituents; and $R^4$ is selected from the group:, halo, —CN, $C_{1-4}$ haloalkyl, $C_{1-4}$ alkyl, phenyl, and benzyl.

[13] In a preferred embodiment, the present invention provides a novel compound of embodiment [1], wherein:

R is H or $NR^1R^2$;

$R^1$ and $R^2$, together with the nitrogen atom to which they are attached, form a 4–8 membered heterocyclenyl group containing an additional 0–1 N, S, or O atom, wherein the heterocyclenyl is substituted with 0–2 $R^4$ substituents; and $R^4$ is selected from the group:, halo, —CN, $C_{1-4}$ haloalkyl, $C_{1-4}$ alkyl, phenyl, and benzyl.

[14] In a preferred embodiment, the present invention provides a novel compound of embodiment [1], wherein:

R is H or $NR^1R^2$;

$R^1$ and $R^2$, together with the nitrogen atom to which they are attached, form a 4–8 membered heterocyclenyl group selected from the group consisting of: 2-pyrrolinyl, 3-pyrrolinyl, 2-imidazolinyl, 2-pyrazolinyl, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, wherein the heterocyclenyl is substituted with 0–2 $R^4$ substituents; and $R^4$ is selected from the group:, halo, —CN, $C_{1-4}$ haloalkyl, $C_{1-4}$ alkyl, phenyl, and benzyl.

[15] In a preferred embodiment, the present invention provides a novel compound of embodiment [1], wherein:

$R^4$ is selected from the group: $C_{1-4}$ haloalkyl, $C_{1-4}$ alkyl, and benzyl.

[16] In a preferred embodiment, the present invention provides a novel compound of embodiment [1], wherein:

$R^4$ is $C_{1-4}$ alkyl.

[17] In a preferred embodiment, the present invention provides a novel compound of embodiment [1], wherein:

$R^4$ is methyl.

[18] In a preferred embodiment, the present invention provides a novel compound of embodiment [1], wherein:

R is NR$^1$R$^2$; and

R$^1$ and R$^2$, together with the nitrogen atom to which they are attached, form a 4–8 membered heterocyclyl group containing an additional 0–1 N, S, or O atom, wherein the heterocyclyl is substituted with a R$^4$ substituent.

[19] In a preferred embodiment, the present invention provides a novel compound of embodiment [1], wherein:

R is NR$^1$R$^2$; and

R$^1$ and R$^2$, together with the nitrogen atom to which they are attached, form a 4–8 membered heterocyclenyl group containing an additional 0–1 N, S, or O atom, wherein the heterocyclenyl is substituted with a R$^4$ substituent.

[20] In a most preferred embodiment, the compounds of this invention are selected from:

3-(2,4-dimethylthiazol-5-yl)-5-(carbamoylamino)indeno[1,2-c]pyrazol-4-one;

3-(2,4-dimethylthiazol-5-yl)-5-(morpholinocarbamoylamino)indeno[1,2-c]pyrazol-4-one;

3-(2,4-dimethylthiazol-5-yl)-5-((1-methyl-1-phenylamino)carbamoylamino)indeno[1,2-c]pyrazol-4-one;

3-(2,4-dimethylthiazol-5-yl)-5-((2,6-dimethylpiperidino) carbamoylamino)indeno[1,2-c]pyrazol-4-one; and 3-(2,4-dimethylthiazol-5-yl)-5-((4-methylpiperazino) carbamoylamino)indeno[1,2-c]pyrazol-4-one;

or stereoisomers thereof, N-Oxides thereof, pharmaceutically acceptable salts thereof, and prodrugs thereof.

[21] Another embodiment of the present invention is a pharmaceutical composition comprising: a pharmaceutically acceptable carrier and a therapeutically effective amount of a compound of embodiment [1].

[22] In another embodiment, the invention describes a pharmaceutical composition, comprising a pharmaceutically acceptable carrier, a compound according to embodiment [1] or a pharmaceutically acceptable salt or prodrug form thereof, and a cytostatic or cytotoxic agent.

[23] In another embodiment, the invention describes a method of treating a cell proliferative disease associated with CDK activity in a patient in need thereof, comprising administrering to said patient a pharmaceutically effective amount of a compound according to embodiment [1], or a pharmaceutically acceptable salt or prodrug form thereof, wherein the proliferative diseases is selected from the group consisting of: Alzheimer's disease, viral infections, autoimmune diseases, fungal disease, cancer, psoriasis, vascular smooth cell proliferation associated with atherosclerosis, pulmonary fibrosis, arthritis glomerulonephritis, neurodegenerative disorders and post-surgical stenosis and restenosis.

[24] In another embodiment, the invention describes a method of treating cancer associated with CDK activity in a patient in need thereof, comprising administrering to said patient a pharmaceutically effective amount of a compound according to embodiment [1], or a pharmaceutically acceptable salt or prodrug form thereof, wherein the cancer is selected from the group consisting of: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoctanthoma, thyroid follicular cancer and Kaposi's sarcoma.

[25] In another embodiment, the invention describes a method of treating a disease associated with apoptosis in a patient in need thereof, comprising administrering to said patient a pharmaceutically effective amount of a compound according to embodiment [1], or a pharmaceutically acceptable salt or prodrug form thereof, wherein the disease associated with apoptosis is selected from the group consisting of: cancer, viral infections, autoimmune diseases and neurodegenerative disorder.

[26] In another embodiment, the invention describes a method of inhibiting tumor angiogenesis and metastasis in a patient in need thereof, comprising administrering to said patient a pharmaceutically effective amount of a compound according to embodiment [1], or a pharmaceutically acceptable salt or prodrug form thereof.

[27] In another embodiment, the invention describes a method of modulating the level of cellular RNA and DNA synthesis in a patient in need thereof, comprising administering to said patient a CDK inhibitory effective amount of a compound according to embodiment [1], or a pharmaceutically acceptable salt or prodrug form thereof.

[28] In another embodiment, the invention describes a method of treating viral infections in a patient in need thereof, comprising administering to said patient a CDK inhibitory effective amount of a compound according to embodiment [1], or a pharmaceutically acceptable salt or prodrug form thereof, wherein the viral infections is selected from the group consiting of HIV, hepatitis, human papilloma virus, herpesvirus, poxvirus, Epstein-Barr virus, Sindbis virus and adenovirus.

[29] In another embodiment, the invention describes a method of chemopreventing cancer in a patient, comprising administering to said patient in need thereof, a CDK inhibitory effective amount of a compound according to embodiment [1], or a pharmaceutically acceptable salt or prodrug form thereof.

[30] In another embodiment, the invention describes a method of inhibiting CDK activity comprising combining an effective amount of a compound according to embodiment [1], with a composition containing CDK.

[31] In another embodiment, the invention describes a method of treating cancer associated with CDK activity in a patient in need thereof, comprising administrering to said patient a pharmaceutically effective amount of a compound according to embodiment [1], or a pharmaceutically acceptable salt or prodrug form thereof, in combination (administered together or sequentially) with known anticancer treatments such as radiation therapy or with cytostatic or cytotoxic agents, wherein such agents are selected from the group consisting of: DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

[32] In another embodiment, the invention describes a method treating cell proliferative diseases associated with CDK activity in a patient in need thereof, comprising administrering to said patient a pharmaceutically effective amount of a compound according to embodiment [1], or a pharmaceutically acceptable salt or prodrug form thereof, in combination (administered together or sequentially) with known anti-proliferating agents selected from the group consisting of:, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPT-11, epothilones , topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, and hydroxyurea.

[33] In another embodiment, the invention describes a method of inhibiting CDK1 activity, comprising adminsitering to a patient in need thereof an efective CDK1 inhibitory amount of a compound according to embodiment [1], or a pharmaceutically acceptable salt or prodrug form thereof.

[34] In another embodiment, the invention describes a method of inhibiting CDK2 activity, comprising adminsitering to a patient in need thereof an efective CDK2 inhibitory amount of a compound according to embodiment [1], or a pharmaceutically acceptable salt or prodrug form thereof.

[35] In another embodiment, the invention describes a method of inhibiting CDK3 activity, comprising adminsitering to a patient in need thereof an efective CDK3 inhibitory amount of a compound according to embodiment [1], or a pharmaceutically acceptable salt or prodrug form thereof.

[36] In another embodiment, the invention describes a method of inhibiting CDK4 activity, comprising adminsitering to a patient in need thereof an efective CDK4 inhibitory amount of a compound according to embodiment [1], or a pharmaceutically acceptable salt or prodrug form thereof.

[37] In another embodiment, the invention describes a method of inhibiting CDK5 activity, comprising adminsitering to a patient in need thereof an efective CDK5 inhibitory amount of a compound according to embodiment [1], or a pharmaceutically acceptable salt or prodrug form thereof.

[38] In another embodiment, the invention describes a method of inhibiting CDK6 activity, comprising adminsitering to a patient in need thereof an efective CDK6 inhibitory amount of a compound according to embodiment [1], or a pharmaceutically acceptable salt or prodrug form thereof.

[39] In another embodiment, the invention describes a method of inhibiting CDK7 activity, comprising adminsitering to a patient in need thereof an efective CDK7 inhibitory amount of a compound according to embodiment [1], or a pharmaceutically acceptable salt or prodrug form thereof.

[40] In another embodiment, the invention describes a method of inhibiting CDK8 activity, comprising adminsitering to a patient in need thereof, an efective CDK8 inhibitory amount of a compound according to embodiment [1], or a pharmaceutically acceptable salt or prodrug form thereof.

[41] In another embodiment, the invention describes a method of inhibiting CDK9 activity, comprising adminsitering to a patient in need thereof an efective CDK9 inhibitory amount of a compound according to embodiment [1], or a pharmaceutically acceptable salt or prodrug form thereof.

[42] In another embodiment, the invention describes a pharmaceutical kit for treating a cell proliferative disease associated with CDK activity, said kit comprising a plurality of separate containers, wherein at least one of said containers contains a compound accordig to embodiment [1], or a pharmaceutically acceptable salt or prodrug form thereof, and at least another of said containers contains one or more compounds selected from the group consisting of cytostatic or cytotoxic agents, such as for example, but not limited to, DNA interactive agents, such as carboplatin, cisplatin or doxorubicin; topoisomerase II inhibitors, such as etoposide; topoisomerase I inhibitors such as CPT-11 or topotecan; tubulin interacting agents, such as paclitaxel, taxane, docetaxel or the epothilones; hormonal agents, such as tamoxifen; thymidilate synthase inhibitors, such as 5-fluorouracil; and anti-metabolites, such as methoxtrexate, and said containers optionally contain a pharmaceutical carrier, which kit may be effectively utilized for carrying out combination therapies according to the invention.

[43] It is a further embodiment of the invention to provide a method of treating a patient having a disorder associated with excessive cell proliferation, comprising administering to the patient a therapeutically effective amount of a compound of embodiment [1], such that the excessive cell proliferation in the patient is reduced.

[44] In another embodiment, the invention describes a enhanced method of inhibiting CDK activity, comprising adminsitering to a patient in need thereof an efective CDK inhibitory amount of a compound according to embodiment [1], or a pharmaceutically acceptable salt or prodrug form thereof.

It is appreciated that certain feactures of the invention, which are, for clarity, described in the context of separate embodiments, may also be provided in combination in a single embodiment. For example, $R^1$ and $R^2$ of embodiment [8] may be combined with $R^4$ of embodiment [16] to form a single embodiment. Conversely, various feactures of the invention which are, for brevity, described in the context of a single embodiment, may also be provided seperately or in any suitable subcombination.

DETAILED DESCRIPTION OF THE INVENTION

As used above, and throughout the description of the invention, the following terms, unless otherwise indicated, shall be understood to have the following meanings:

Definitions

As used herein, the following terms and expressions have the indicated meanings.

The term "compounds of the invention", and equivalent expressions, are meant to embrace compounds of the invention as herein before described i.e. compounds of formula (I), which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "effective amount" means an amount of a compound/composition according to the present invention effective in producing the desired therapeutic effect.

The term "amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

The term "acid labile amine protecting group" means an amine protecting group as defined above which is readily removed by treatment with acid while remaining relatively stable to other reagents. A preferred acid labile amine protecting group is tert-butoxycarbonyl (BOC).

The term "hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

The term "hydrogenation labile acid protecting group" means an acid protecting group as defined above which is readily removed by hydrogenation while remaining relatively stable to other reagents. A preferred hydrogenation labile acid protecting group is benzyl.

The term "analogue" means a compound which comprises a chemically modified form of a specific compound or class thereof, and which maintains the pharmaceutical and/or pharmacological activities characteristic of said compound or class.

The term "patient" includes both human and other mammals.

The term "pharmaceutical composition" means a composition comprising a compound of formula (I) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

The term "solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkythio, thioester, sulfonyl, nitro, heterocyclo, aryl or heteroaryl. It will also be understood by those skilled in the art that the substituted moieties themselves can be substituted as well when appropriate.

The terms "halo" or "halogen" as used herein refer to fluoro, chloro, bromo and iodo. The term "aryl" is intended to mean an aromatic moiety containing the specified number of carbon atoms, such as, but not limited to phenyl, indanyl or naphthyl. The terms "cycloalkyl" and "bicycloalkyl" are intended to mean any stable ring system, which may be saturated or partially unsaturated. Examples of such include, but are not limited to, cyclopropyl, cyclopentyl, cyclohexyl, norbornyl, bicyclo[2.2.2]nonane, adamantly, or tetrahydronaphthyl (tetralin).

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a heterocyclyl, heterocycleny, or heteroaryl groups as described herein, which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and Spiro compounds containing, for example, the above heterocycles.

"Heterocyclenyl" means a non-aromatic monocyclic or multicyclic hydrocarbon ring system of about 3 to about 10 atoms, preferably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of rings of the ring system include about 5 to about 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or $R^4$ substitents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc. ", 82:5566 (1960). Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydrofuranyl. Preferred is dihydrofuranyl. An exemplary multicyclic oxaheterocyclenyl group is 7-oxabicyclo[2.2.1]heptenyl. Preferred monocyclic thiaheterocycleny rings include dihydrothiophenyl and dihydtothiopyranyl; more preferred is dihydrothiophenyl.

"Heterocyclyl" means a non-aromatic saturated monocyclic or multicyclic ring system of about 3 to about 10 carbon atoms, preferably about 4 to about 8 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more $R^4$ substituents which may be the same or different, and are as defined herein. The nitrogen or sulphur atom of the heterocyclyl may also be optionally oxidized to the corresponding N-oxide, S-oxide or S,S-dioxide. "Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" means an aromatic monocyclic or multicyclic ring system of about 5 to about 10 atoms, in which one or more of the atoms in the ring system is/are hetero element(s) other than carbon, for example nitrogen, oxygen or sulfur. Preferred ring sizes of rings of the ring system include about 5 to about 6 ring atoms. The "heteroaryl" may also be substituted by one or more R4 subsituents which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc. ", 82:5566 (1960). Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo [2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. Preferred heteroaryl groups include pyrazinyl, thienyl, pyridyl, pyrimidinyl, isoxazolyl and isothiazolyl.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

The term "Treating" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

PREPARATION OF COMPOUNDS OF THE INVENTION

It will be apparent to those skilled in the art that certain compounds of formula (I) can exhibit isomerism, for example geometrical isomerism, e.g., E or Z isomerism, and optical isomerism, e.g., R or S configurations. Geometrical isomers include the cis and trans forms of compounds of the invention having alkenyl moieties. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on CDK inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on CDK inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are more likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

Preferred methods of synthesizing the compounds of the invention include, but are not limited to, those methods described below. Additional methods for synthesizing the compounds of this invention can be found in WO 99/54308 which is incorporated herein in its entirety. Each of the references cited below are hereby incorporated herein by reference.

The compounds of formula I can be prepared by the chemistry described in Scheme 1. 2,4-Dimethyl-5-acetylthiazole was converted to the 1,3-diketone 2 by treatment with sodium ethoxide and ethyl trifluoroacetate. Condensation of diketone 2 with 3-nitrophthalic anhydride (3) using the conditions described in Rotberg and Oshkaya, Zh. Organ. Khim. 8:84–87, 1972; Zh. Organ. Khim. 9:2548–2550, 1973, the contents of which are hereby incorporated herein by reference, gave nitrotriketone 4. Additional means of preparing triketones are known to one skilled in the art as described in Kilgore et al, Industrial and Engineering Chemistry 34:494–497, 1946, the contents of which are hereby incorporated herein by reference. Reduction of the nitro to the aniline (5) was effected using zinc and calcium chloride. The aniline (5) was reacted with phenyl chloroformate and the resulting carbamate 6 was converted to the semicarbazide using the appropriate hydrazine. The triketone was converted to the indeno[1,2-c]pyrazol-4-one ring system (I) with hydrazine in refluxing ethanol. Additional means of preparing indeno[1,2-c]pyrazol-4-ones are known to one skilled in the art as described in Lemke et al., J. Heterocyclic Chem. 19:1335–1340, 1982; Mosher and Soeder, J. Heterocyclic Chem. 8:855–59, 1971; Hrnciar and Svanygova Collect. Czech. Chem. Commun. 59:2734–40, 1994 the contents of which are hereby incorporated herein by reference.

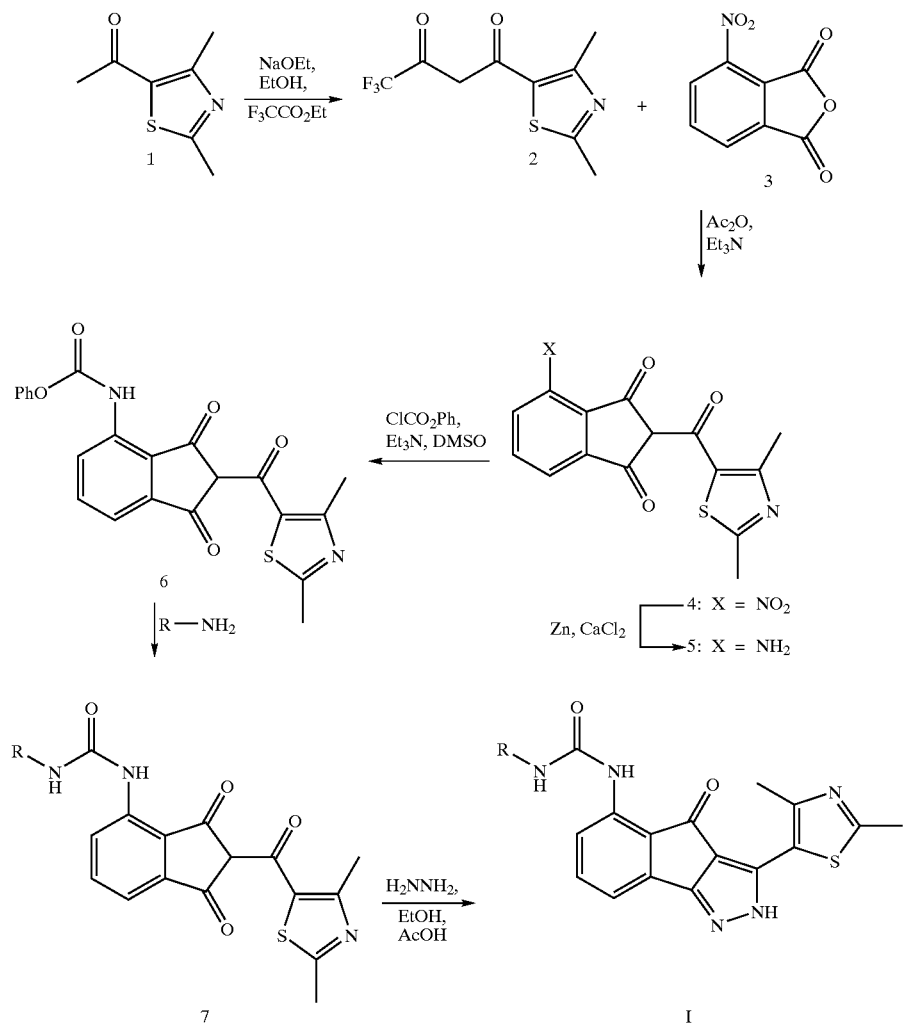

An alternative method for making compounds of the present invention is shown in Scheme 2. The intermediate aniline 5 can be acetylated and cyclized to the pyrazole 9 using the same conditions previously described in Scheme 1. Removal of the acetyl group with strong acid followed by protection of the pyrazole nitrogen gave aniline 11. Conversion of the aniline (11) to the phenyl carbamate 12 followed by treatment with the appropriate hydrazine gave the protected semicarbazide 13. Removal of the 2-(trimethylsilyl)ethoxymethyl (SEM) protecting group using hydrochloric acid provided the pyrazole (I).

Another method for making compounds of the present invention is presented in Scheme 3. Aniline 5 can be directly converted to the semicarbazide 7 using the preformed carbamate 14. Reagents such as 14 are readily prepared in advance by one skilled in the art using the appropriate hydrazine and phenyl chloroformate. Cyclization of the triketone 7 proceeded as previously described in Scheme 1.

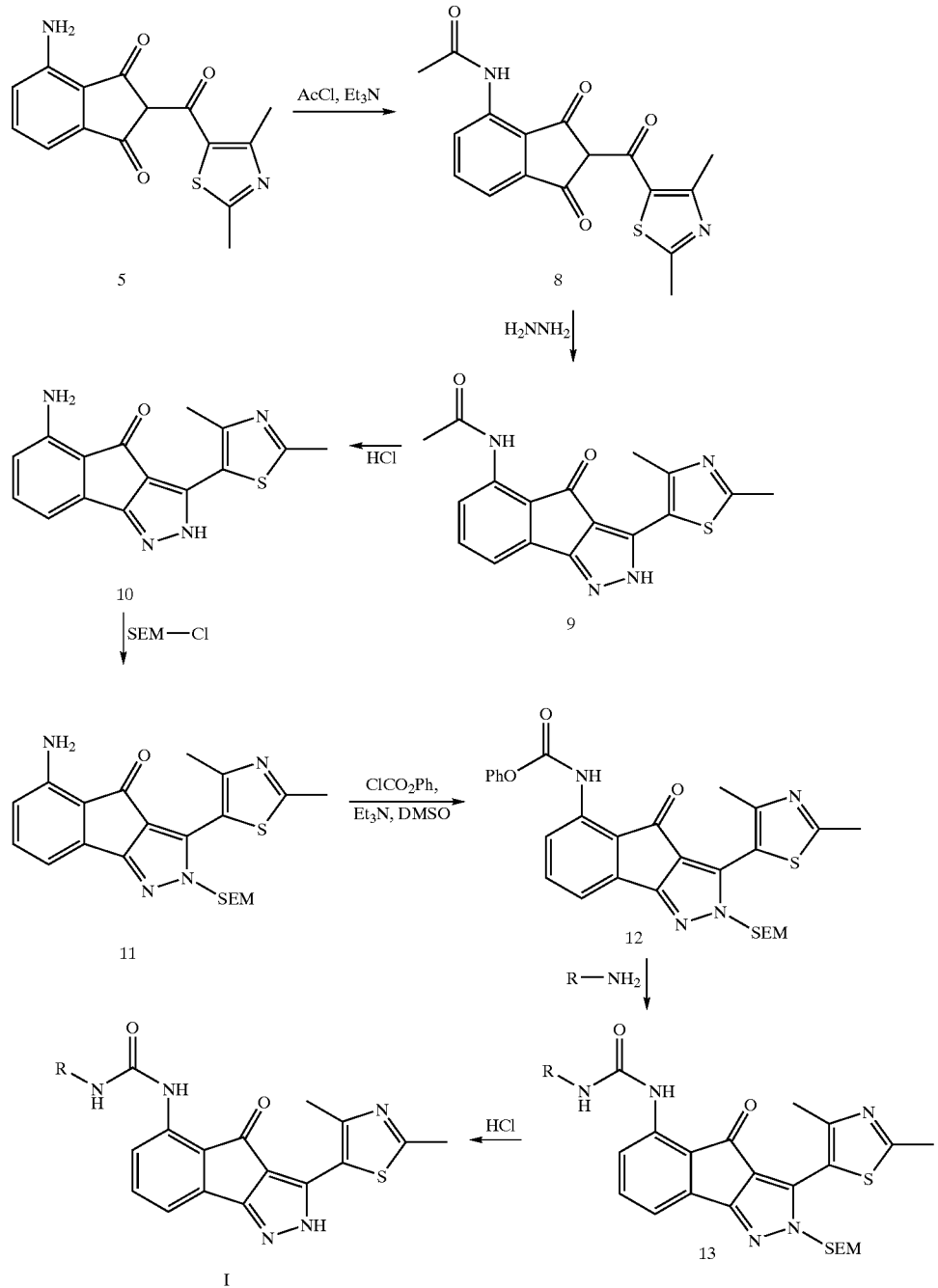

Scheme 2

Scheme 3

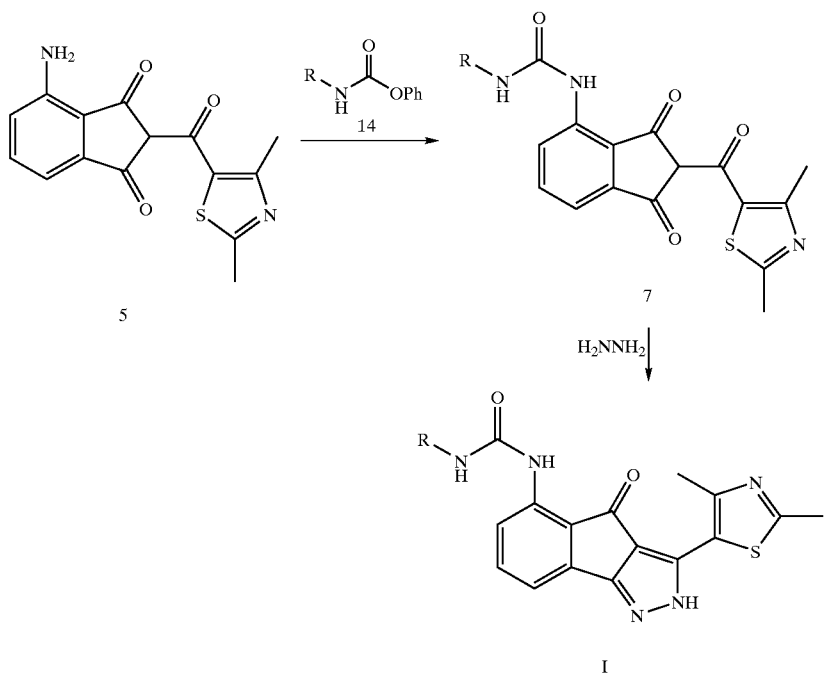

EXAMPLES

Abbreviations used in the Examples are defined as follows: "° C." for degrees Celsius, "ESI-MS" for electrospray ionization mass spectroscopy, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography.

Example 1

Preparation of 3-(2,4-dimethylthiazol-5-yl)-5-(carbamoylamino)indeno[1,2-c]pyrazol-4-one

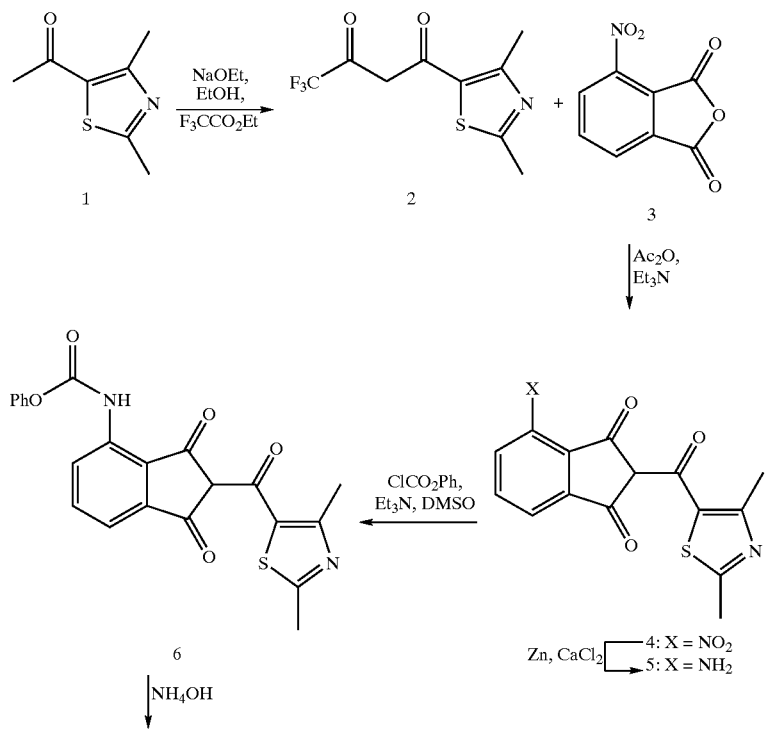

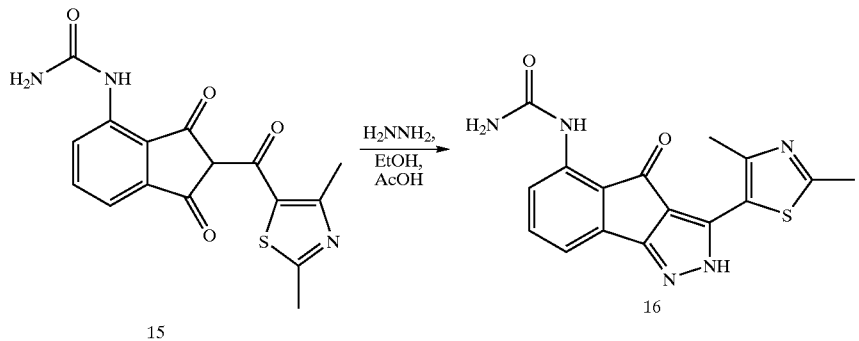

Step 1. Synthesis of Nitrotriketone 4 from 1.

Ethyl trifluoroacetate (22.9 g, 161 mmol) and 2,4-dimethyl-5-acetylthiazole (25.0 g, 161 mmol) were added to a solution of sodium ethoxide, freshly prepared from sodium (3.71 g, 161 mmol) and ethanol (500 mL), and stirred at 23° C. for 12 h. Half of the volume of organic solvent was concentrated in vacuo and the reaction mixture was diluted with 6 M HCl (400 mL) and extracted with ethyl acetate (2×300 mL). The combined organic extracts were washed with brine (2×300 mL), dried (MgSO$_4$), filtered, and concentrated in vacuo to give 1,3-diketone 2 as an orange oil which was used without purification. 3-Nitrophthalic anhydride (31.1 g, 161 mmol) was added to a solution of diketone 2 in acetic anhydride (91.2 mL, 968 mmol). The reaction mixture was cooled to 0° C. and triethylamine (67.3 mL, 484 mmol) was added dropwise over 1 h. The reaction mixture was warmed to 23° C. and stirred for 12 h, heated to 50° C. for 30 min, and then cooled to 23° C. The reaction mixture was slowly poured into 1 M HCl (484 mL, diluted with 1 L of water). The solid which precipitated was filtered and washed repeatedly with water (3×150 mL) to give a brown solid (24.4 g, 46%, 2 steps). ESI-MS (M−H) found for $C_{15}H_9N_2O_5S$: 329.

Step 2. Synthesis of Aniline 5 from 4.

A solution of nitrotriketone 4 (24.4 g, 73.9 mmol), zinc powder (160 g, 2.4 mol), and calcium chloride (5.3 g, 48 mmol) in 4:1 ethanol/water (370 mL) was heated to reflux for 1 h. The reaction mixture was filtered over celite and washed with methanol (3×150 mL) and ethyl acetate (3×150 mL). The filtrate was concentrated in vacuo to give a crude brown solid. Purification by flash column chromatography (silica, chloroform→2% methanol/chloroform→5% methanol/chloroform→7% methanol/chloroform) gave aniline 5 (13.0 g, 59%) as a brown solid. ESI-MS (M−H) found for $C_{15}H_{11}N_2O_3S$: 299.

Step 3. Synthesis of Carbamate 6 from 5.

A solution of aniline 5 (840 mg, 2.8 mmol), phenyl chloroformate (0.42 mL, 3.4 mmol), and sodium carbonate (1.6 g) in acetone (14 mL) was heated to 50° C. for 4 h. The reaction mixture was cooled to 23° C. and diluted with water (20 mL) and ethyl acetate (20 mL). The organic layer was separated and washed with brine (20 mL), dried (MgSO4), filtered, and concentrated in vacuo to give a crude brown solid. Trituration with ether gave carbamate 6 (1.18 g, 99%) as a brown solid. ESI-MS (M−H) found for $C_{22}H_{15}N_2O_5S$: 419.

Step 4. Synthesis of Urea 15 from 6.

A solution of carbamate 6 (1.18 g, 2.8 mmol) and ammonium hydroxide (0.47 mL, 3.4 mmol) in N,N-dimethylformamide (5 mL) was heated to 90° C. for 1 h. The solvent was concentrated in vacuo to give a crude residue. Purification using reverse phase HPLC (acetonitrile/water/trifluoroacetic acid) gave the product as a yellow solid (117 mg, 12%). ESI-MS (M−H) found for $C_{16}H_{12}N_3O_4S$: 342.

Step 5. Synthesis of Pyrazole 16 from 15.

A solution of urea 15 (117 mg, 0.34 mmol), hydrazine (21 μL, 0.68 mmol), and p-toluenesulfonic acid (3.2 mg, 17 μmol) in ethanol (1.7 mL) was refluxed for 4 h. The reaction mixture was cooled to 23° C. and concentrated in vacuo to give a crude residue. Purification using reverse phase HPLC (acetonitrile/water/trifluoroacetic acid) gave the product as its TFA-salt (10 mg, 9%). ESI-MS (M+H) calc'd for $C_{16}H_{14}N_5O_2S$: 340.0868, found: 340.0895.

Example 2

Preparation of 3-(2,4-dimethylthiazol-5-yl)-5-(morpholinocarbamoylamino)indeno[1,2-c]pyrazol-4-one

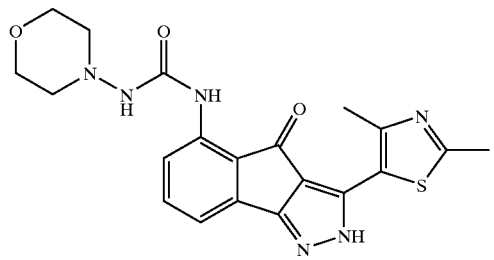

Prepared in a similar fashion as described for example 1 using 6 and morpholine as the starting materials. mp >300° C. (TFA salt); ESI-MS (M+H) calc'd for $C_{20}H_{21}N_6O_3S$: 425.1396, found: 425.1424.

Example 3

Preparation of 3-(2,4-dimethylthiazol-5-yl)-5-((1-methyl-1-phenylamino) carbamoylamino) indeno [1,2-c]pyrazol-4-one

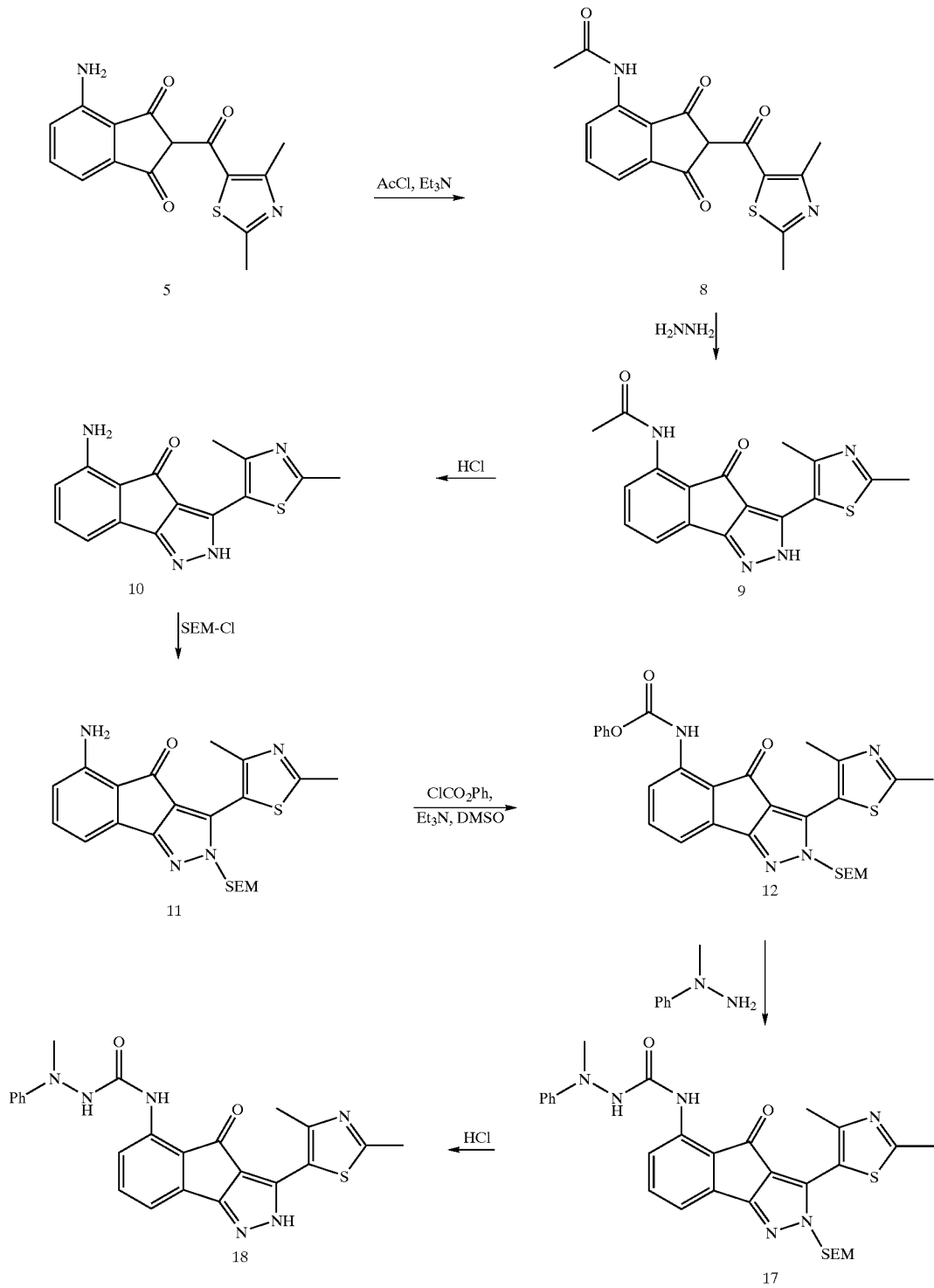

Step 1. Synthesis of Acetamide 8 from 5.

A solution of aniline 5 (3.3 g, 10.8 mmol) in N,N-dimethylformamide (54 mL) was treated with acetyl chloride (0.81 mL, 11.4 mmol) and triethylamine (1.7 mL, 11.9 mmol) and refluxed for 4 h. The reaction mixture was cooled to 23° C. and diluted with ethyl acetate (100 mL) and water (100 mL). The aqueous layer was separated and washed with ethyl acetate (100 mL). The combined organic extracts were washed with brine (100 mL), dried (MgSO$_4$), filtered, and concentrated in vacuo to give a crude brown solid. The solid was dissolved in a small amount of methylene chloride (~10 mL) and treated with ether. The solid which precipatated was filtered and washed with ether (3×100 mL) to give a brown solid (1.6 g, 43%). ESI-MS (M−H) found for C$_{17}$H$_{13}$N$_2$O$_4$S: 341.

Step 2. Synthesis of Pyrazole 9 from 8.

A solution of triketone 8 (1.6 g, 4.7 mmol), hydrazine (0.71 mL, 9.4 mmol), and p-toluenesulfonic acid (44 mg, 0.23 mmol) in ethanol (23 mL) was refluxed for 4 h. The reaction mixture was cooled to 23° C. and the solid was filtered and washed with ethanol (20 mL) and ether (20 mL). Recrystalization of the precipatate from ethanol gave the product as a brown solid (400 mg, 25%). ESI-MS (M−H) found for $C_{17}H_{13}N_4O_2S$: 337.

Step 3. Synthesis of Aniline 10 from 9.

A solution of pyrazole 9 (400 mg, 1.2 mmol) and concentrated hydrochloric acid (2 mL) in methanol was refluxed for 3 h. The reaction mixture was cooled to 23° C. and concentrated in vacuo to give the product as a yellow solid (350 mg, 99%). ESI-MS (M−H) found for $C_{15}H_{11}N_4OS$: 295.

Step 4. Synthesis of Aniline 11 from 10.

A solution of aniline 10 (350 mg, 1.2 mmol) in dioxane (6 mL) was treated with triethylamine (0.69 mL, 5 mmol) and 2-(trimethylsilyl)ethoxymethyl chloride (0.52 mL, 3 mmol) and heated to reflux for 3 h. The reaction mixture was cooled to 23° C. and diluted with EtOAc (20 mL) and water (20 mL). The aqueous layer was separated and extracted with ethyl acetate (20 mL). The combined organic extracts were washed with brine (20 mL), dried (MgSO$_4$), filtered, and concentrated in vacuo to give a yellow solid. The yellow solid was treated with methylene chloride (50 mL) and methanol (50 mL) and filtered. The filtrate was concentrated in vacuo to give a crude brown residue. Purification by flash column chromatography (silica, 10% ethyl acetate/hexane→20% ethyl acetate/hexane→40% ethyl acetate/hexane→80% ethyl acetate/hexane) gave aniline 11 (235 mg, 47%) as a brown solid. ESI-MS (M+H) found for $C_{21}H_{27}N_4O_2SSi$: 427.

Step 5. Synthesis of Carbamate 12 from 11.

Prepared in a similar fashion as described for example 1, step 3, using aniline 11 as the starting material. ESI-MS (M+H) found for $C_{28}H_{31}N_4O_4SSi$: 547.

Step 6. Synthesis of Pyrazole 17 from 12.

A solution of carbamate 12 (167 mg, 0.3 mmol) and 1-methyl-1-phenylhydrazine (72 μL, 0.6 mmol) in dimethyl sulfoxide (2 mL) was heated to 90° C. for 1 h. The solvent was concentrated in vacuo to give a crude residue which was diluted with 1:1 acetonitrile/water (3 mL). The solid which precipitated was filtered to give the product as a yellow solid (110 mg, 63%). ESI-MS (M+H) found for $C_{29}H_{35}N_6O_3SSi$: 574.

Step 7. Synthesis of Pyrazole 18 from 17.

A solution of 17 (110 mg, 0.2 mmol) in ethanol (10 mL) was treated with 4M hydrochloric acid in dioxane (10 mL) and heated to 70° C. for 1 h. The reaction mixture was cooled to 23° C. and the solid which precipitated was filtered to give the product as its HCl-salt (50 mg, 59%). mp=250° C.; ESI-MS (M+H) calc'd for $C_{23}H_{21}N_6O_2S$: 445.1447, found: 445.1432.

Example 4

Preparation of 3-(2,4-dimethylthiazol-5-yl)-5-((2,6-dimethylpiperidino)carbamoylamino)indeno[1,2-c]pyrazol-4-one

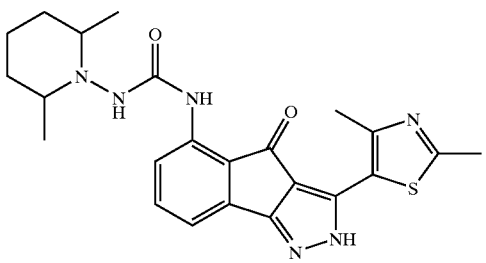

Prepared in a similar fashion as described for example 3 using 12 and 1-amino-2,6-dimethylpiperidine as the starting materials. ESI-MS (M+H) found for $C_{23}H_{37}N_6O_2S$: 451.

Example 5

Preparation of 3-(2,4-dimethylthiazol-5-yl)-5-((4-methylpiperazino)carbamoylamino)indeno[1,2-c]pyrazol-4-one

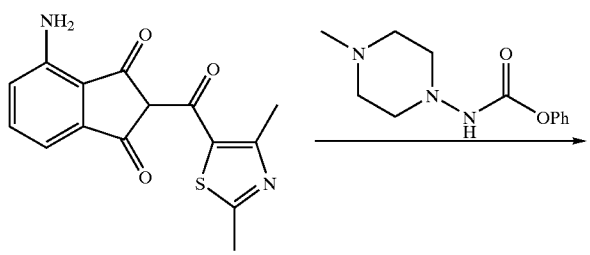

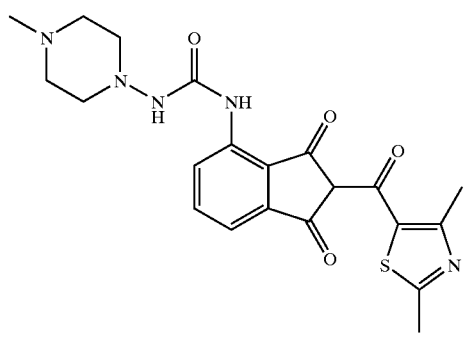

-continued

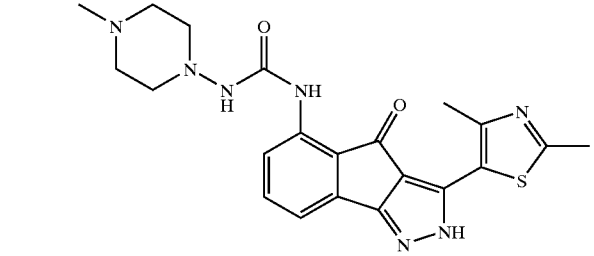

20

Step 1. Synthesis of Semicarbazide 19 from aniline 5.

A solution of aniline 5 (13.0 g, 43.3 mmol), N-(4-methylpiperazinyl)-O-(phenyl)carbamate (20.4 g, 86.7 mmol), and triethylamine (18.1 mL, 130 mmol) in dimethylsulfoxide (217 mL) was heated to 90° C. for 1 h. The reaction mixture was cooled to 23° C. and diluted with water (500 mL). The solid which precipitated was collected and washed with water (300 mL), ethanol (300 mL), and ether (300 mL) and dried to give a brown solid (15.6 g, 82%). ESI-MS (M+H) calc'd for $C_{21}H_{24}N_5O_4S$: 442.1549, found: 442.1531.

Step 2. Synthesis of Pyrazole 20 from Semicarbazide 19.

A solution of semicarbazide 19 (15.6 g, 35.3 mmol), hydrazine (6.7 mL, 212 mmol), and acetic acid (4.0 mL, 71 mmol) was refluxed in ethanol (354 mL) for 84 h. The reaction mixture was cooled to 23° C., filtered, washed with ethanol (300 mL) and ether (300 mL), and dried to give a yellow solid which was dissolved in 10% acetic acid in water (20 mL). The solution was adjusted to pH=7 with 10% sodium hydroxide. The solid which precipitated was filtered and dried to give the free base (6.8 g, 29%) as a yellow solid. The free base was dissolved in 1M hydrochloric acid (31 mL) and the water was removed with a lyophilizer to give the product as a light brown powder (7.9 g, 99% from the free base). mp=278° C.; ESI-MS (M+H) calc'd for $C_{21}H_{24}N_7O_2S$: 438.1712, found: 438.1714.

UTILITY

Inhibition of Kinase/Cyclin Complex Enzymatic Activity

The compounds of this invention were assayed for their inhibitory activity against CDK2/E kinase complexe (see WO 99/54308 for descriptions of these assays).

Inhibition of HCT 116 Cancer Cell Proliferation

The cellular activity of the compounds disclosed in this invention were examined using cultured HCT116 cells (see WO 99/54308 for descriptions of this assay).

Inhibition of AG1523 Fibroblast Cells

To test the ability of several compounds disclosed in this invention to kill arrested, normal human cells, we examined the effect of these compounds on cultured AG1523 cells, a human foreskin fibroblast primary cell line. This assay was designed such that a decrease in absorbance, as measured by a cytotoxicity test using 3-(4,5-dimethylthiazol-2-yl)-2,5-diphenyltetrazolium bromide (MTT) as an indicator of metabolic activity (Carmichael, James et al. "Evaluation of a Tetrazolium-based Semiautomated Colorimetric Assay: Assesment of Chemosensitivity Testing." Cancer Research 47, 936–942, Feb. 15, 1987), is observed in treated cells only in the event that the treated cells undergo death. Briefly, AG1523 cells are cultured as confluent monolayers which are G1-arrested due to contact inhibition in the presence of test compounds at increasing concentrations. At selected time points, MTT is added to groups of cells. Mitochondrial dehydrogenase of viable cells reduced the MTT to a blue formazan product which was solubilized in 0.04N HCl in isopropyl alcohol and measured spectrophotometrically

What is claim is:

1. A novel compound of formula (I):

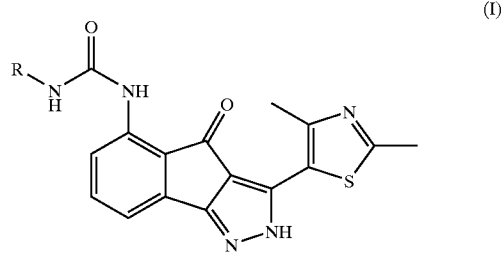

(I)

or stereoisomers thereof, N-Oxides thereof, pharmaceutically acceptable salts thereof, and prodrugs thereof, wherein:

R is independently at each occurrence selected from the group: H, $NR^1R^2$, $NR^1C(O)R^3$, $NR^1C(O)OR^5$, $NHC(O)NR^1R^2$, $NHC(S)NR^1R^2$, and 5–10 membered heterocycle containing from 1–4 heteroatoms selected from O, N, and S, wherein the heterocycle is substituted with 0–4 $R^4$ substituents;

$R^1$ is selected from the group: H, halo, —CN, $C_{1-4}$ haloalkyl, $C_{1-4}$ alkyl, phenyl, and benzyl;

$R^2$ is selected from the group: H, $C_{1-4}$ alkyl, phenyl, and benzyl;

alternatively, $R^1$ and $R^2$, together with the nitrogen atom to which they are attached, form a 4–8 membered heterocyclic group or a 4–8 membered heterocyclenyl group containing an additional 0–1 N, S, or O atom, wherein the heterocyclic or heterocyclenyl group is substituted with 0–4 $R^4$ substituents;

$R^3$ is selected from the group: H, halo, —CN, $C_{1-4}$ haloalkyl, $C_{1-4}$ alkyl, phenyl, and benzyl; and $R^4$ is selected from the group: halo, —CN, $C_{1-4}$ haloalkyl, $C_{1-4}$ alkyl, phenyl, and benzyl;

$R^5$ is selected from the group: H, $C_{1-4}$ alkyl, phenyl, and benzyl.

2. A compound according to claim 1, wherein: R is a 5–10 membered heterocycle containing from 1–4 heteroatoms selected from O, N, and S, wherein the heterocycle is substituted with 0–3 $R^4$ substituents.

3. A compound according to claim 1, wherein: R is a 5–10 membered heterocycle containing from 1–4 heteroatoms selected from O, N, and S, wherein the heterocycle is substituted with 0–2 $R^4$ substituents.

4. A compound according to claim 1, wherein: R is a 5–10 membered heterocycle containing from 1–4 heteroatoms selected from O, N, and S, wherein the heterocycle is substituted with a $R^4$ substituent.

5. A compound according to claim 1, wherein: R is a 5–6 membered hetroaryl, heterocyclyl, or heterocyclenyl group, substituted with 0–3 $R^4$ substituents.

6. A compound according to claim 1, wherein:

R is H or $NR^1R^2$;

$R^1$ is selected from the group: H, $C_{1-4}$ alkyl, phenyl, and benzyl;

$R^2$ is selected from the group: H, $C_{1-4}$ alkyl, phenyl, and benzyl;

alternatively, $R^1$ and $R^2$, together with the nitrogen atom to which they are attached, form a 4–8 membered heterocyclic group or a 4–8 membered heterocyclenyl group containing an additional 0–1 N, S, or O atom, wherein the heterocyclic or heterocyclenyl group is substituted with 0–3 $R^4$ substituents; and $R^4$ is selected from the group: halo, —CN, $C_{1-4}$ haloalkyl, $C_{1-4}$ alkyl, phenyl, and benzyl.

7. A compound according to claim 1, wherein: R is H or $NR^1R^2$; $R^1$ is selected from the group: H, $C_{1-4}$ alkyl, phenyl, and benzyl; and $R^2$ is selected from the group: H, $C_{1-4}$ alkyl, phenyl, and benzyl.

8. A compound according to claim 1, wherein:

R is H or $NR^1R^2$;

$R^1$ and $R^2$, together with the nitrogen atom to which they are attached, form a 4–8 membered heterocyclic group containing an additional 0–1 N, S, or O atom, wherein the heterocyclic is substituted with 0–3 $R^4$ substituents; and $R^4$ is selected from the group: halo, —CN, $C_{1-4}$ haloalkyl, $C_{1-4}$ alkyl, phenyl, and benzyl.

9. A compound according to claim 1, wherein: R is H or $NR^1R^2$; $R^1$ and $R^2$, together with the nitrogen atom to which they are attached, form a 4–8 membered heterocyclyl group containing an additional 0–1 N, S, or O atom, wherein the heterocyclyl is substituted with 0–2 $R^4$ substituents; and $R^4$ is selected from the group:, halo, —CN, $C_{1-4}$ haloalkyl, $C_{1-4}$ alkyl, phenyl, and benzyl.

10. A compound according to claim 1, wherein:

$R^1$ and $R^2$, together with the nitrogen atom to which they are attached, form a heterocyclyl group selected from the group consisting of pyrrolidinyl, imidazolidinyl, pyrazolidinyl, piperidinyl, morpholinyl, thiomorpholinyl, and piperazinyl, wherein the heterocyclyl is substituted with 0–3 $R^4$ substituents; and $R^4$ is selected from the group: halo, —CN, $C_{1-4}$ haloalkyl, $C_{1-4}$ alkyl, phenyl and benzyl.

11. A compound according to claim 1, wherein:

$R^1$ and $R^2$, together with the nitrogen atom to which they are attached, form a heterocyclyl group selected from the group consisting of piperidinyl, morpholinyl, and piperazinyl, wherein the heterocyclyl is substituted with 0–3 $R^4$ substituents; and $R^4$ is selected from the group: halo, —CN, $C_{1-4}$ haloalkyl, $C_{1-4}$ alkyl, phenyl, and benzyl.

12. A compound according to claim 1, wherein: R is H or $NR^1R^2$; $R^1$ and $R^2$, together with the nitrogen atom to which they are attached, form a 4–8 membered heterocyclenyl group containing an additional 0–1 N, S, or O atom, wherein the heterocyclenyl is substituted with 0–3 $R^4$ substituents; and $R^4$ is selected from the group:, halo, —CN, $C_{1-4}$ haloalkyl, $C_{1-4}$ alkyl, phenyl, and benzyl.

13. A compound according to claim 1, wherein: R is H or $NR^1R^2$; $R^1$ and $R^2$, together with the nitrogen atom to which they are attached, form a 4–8 membered heterocyclenyl group containing an additional 0–1 N, S, or O atom, wherein the heterocyclenyl is substituted with 0–2 $R^4$ substituents; and $R^4$ is selected from the group:, halo, —CN, $C_{1-4}$ haloalkyl, $C_{1-4}$ alkyl, phenyl, and benzyl.

14. A compound according to claim 1, wherein: R is H or $NR^1R^2$; $R^1$ and $R^2$, together with the nitrogen atom to which they are attached, form a 4–8 membered heterocyclenyl group selected from the group consisting of: 2-pyrrolinyl, 3-pyrrolinyl, 2-imidazolinyl, 2-pyrazolinyl, 1,2,3,4-tetrahydrohydropyridine, 1,2-dihydropyridyl, 1,4-dihydropyridyl, 1,2,3,6-tetrahydropyridine, 1,4,5,6-tetrahydropyrimid-ine, wherein the heterocyclenyl is substituted with 0–2 $R^4$ substituents; and $R^4$ is selected from the group:, halo, —CN, $C_{1-4}$ haloalkyl, $C_{1-4}$ alkyl, phenyl, and benzyl.

15. A compound according to claim 1, wherein: $R^4$ is selected from the group: $C_{1-4}$ haloalkyl, $C_{1-4}$ alkyl, and benzyl.

16. A compound according to claim 1, wherein: R is $C_{1-4}$ alkyl.

17. A compound according to claim 1, wherein: $R^4$ is methyl.

18. A compound according to claim 1, wherein: R is $NR^1R^2$; and $R^1$ and $R^2$, together with the nitrogen atom to which they are attached, form a 4–8 membered heterocyclyl group containing an additional 0–1 N, S, or O atom, wherein the heterocyclyl is substituted with a $R^4$ substituent.

19. A compound according to claim 1, wherein: R is $NR^1R^2$; and $R^1$ and $R^2$, together with the nitrogen atom to which they are attached, form a 4–8 membered heterocyclenyl group containing an additional 0–1 N, S, or O atom, wherein the heterocyclenyl is substituted with a $R^4$ substituent.

20. A compound according to claim 1, selected from the group consisting of:

3-(2,4-dimethylthiazol-5-yl)-5-(carbamoylamino)indeno [1,2-c]pyrazol-4-one;

3-(2,4-dimethylthiazol-5-yl)-5-(morpholinocarbamoylamino)indeno[1,2-c]pyrazol-4-one;

3-(2,4-dimethylthiazol-5-yl)-5-((1-methyl-1-phenylamino)carbamoylamino)indeno[1,2-c]pyrazol-4-one; 3-(2,4-dimethylthiazol-5-yl)-5-((2,6-dimethylpiperidino)carbamoylamino) indeno[1,2-c] pyrazol-4-one; and 3-(2,4-dimethylthiazol-5-yl)-5-((4-methylpiperazino)carbamoylamino)indeno[1,2-c] pyrazol-4-one;

or stereoisomers thereof, N-Oxides thereof, pharmaceutically acceptable salts thereof, and prodrugs thereof.

21. A pharmaceutical composition comprising: a pharmaceutically acceptable carrier and a therapeutically effective amount of a compound of claim 1.

22. A pharmaceutical composition, comprising a pharmaceutically acceptable carrier, a compound according to claim 1 or a pharmaceutically acceptable salt or prodrug form thereof, and a cytostatic or cytotoxic agent.

* * * * *